(12) United States Patent
Wray

(10) Patent No.: US 6,763,730 B1
(45) Date of Patent: Jul. 20, 2004

(54) VIBRATING TUBE METER

(75) Inventor: Troy Wray, Stonehouse (GB)

(73) Assignee: ABB Limited, Staffordshire (GB)

( * ) Notice: Subject to any disclaimer, the term of this patent is extended or adjusted under 35 U.S.C. 154(b) by 0 days.

(21) Appl. No.: 09/979,636

(22) PCT Filed: May 22, 2000

(86) PCT No.: PCT/GB00/01967

§ 371 (c)(1),
(2), (4) Date: Mar. 11, 2002

(87) PCT Pub. No.: WO00/71979

PCT Pub. Date: Nov. 30, 2000

(30) Foreign Application Priority Data

May 25, 1999 (GB) .............................. 9912177

(51) Int. Cl.[7] .............................................. G01F 1/84
(52) U.S. Cl. ............................ 73/861.356; 73/861.355; 73/861.357
(58) Field of Search .............. 73/861.355–861.357, 73/861, 861.01–861.03, 861.18–861.31, 170.07–170.11, 170.13, 155; 137/455, 101.19, 101.21, 115.03–115.06, 87.03, 88

(56) References Cited

U.S. PATENT DOCUMENTS

| 4,192,184 A | 3/1980 | Cox et al. | |
|---|---|---|---|
| RE31,450 E | 11/1983 | Smith | |
| 4,422,338 A | 12/1983 | Smith | |
| 4,711,132 A | * 12/1987 | Dahlin | 73/861.356 |
| 4,856,346 A | 8/1989 | Kane | |
| 5,005,400 A | 4/1991 | Lew | |
| 5,394,758 A | 3/1995 | Wenger et al. | |
| 5,423,221 A | 6/1995 | Kane et al. | |
| 5,473,949 A | 12/1995 | Cage et al. | |
| 5,497,665 A | * 3/1996 | Cage et al. | 73/861.356 |
| 5,533,381 A | * 7/1996 | Seale | 73/19.03 |
| 5,753,827 A | 5/1998 | Cage | |

FOREIGN PATENT DOCUMENTS

| EP | 0 701 107 A3 | 12/1996 |
|---|---|---|
| EP | 0 816 807 A2 | 1/1998 |
| WO | WO 92/14123 A1 | 8/1992 |
| WO | WO 98/07009 | 2/1998 |

* cited by examiner

*Primary Examiner*—Edward Lefkowitz
*Assistant Examiner*—Alandra N. Ellington
(74) *Attorney, Agent, or Firm*—Stites & Harbison, PLLC; Ross F. Hunt, Jr.

(57) ABSTRACT

In a vibrating tube meter such as a Coriolis meter, an accurate measurement of a fluid parameter such as density can be obtained, substantially independent of stress, by measuring vibrational characteristics, particular resonant frequencies of two different vibrational modes. Stress or other variables can be determined from the measurement. Because the measurement of or compensation for stress is based directly on the vibrational characteristics, better accuracy may be obtained than by using a conventional strain gauge to measure stress. The techniques disclosed can give accurate results without requiring particular constraints on meter design.

62 Claims, 10 Drawing Sheets

VIBRATING TUBE METER

The present invention relates to meters which derive a measurement by vibrating a metering tube, particularly Coriolis-type flow meters, such as are described in U.S. Pat. No. 4,422,338, U.S. Pat. No. 5,423,221, U.S. Pat. No. 4,856,346, U.S. Pat. No. 5,394,758, U.S. Pat. No. 4,192,184 and U.S. Re. Pat. No. 31,450, the disclosures of each of which are herein incorporated by reference. The invention is also applicable to other meters, for example densitometers which operate by vibrating a metering tube.

Coriolis meters may be used to obtain a measure of mass flow rate, from the phase difference between sensor outputs and also a measure of density, from the resonant frequency. Pursuant to the invention, we have found that density measurements in conventional meters may be inaccurate, particularly when the stress in the metering tube varies, for example when the meter is subjected to a change in temperature, either ambient temperature or temperature of process fluid. The problem is particularly acute in straight, or nearly straight, tube meters, where we have found that uncompensated errors of tens of percent and even compensated errors of several percent may arise in the event of a change in process fluid temperature in a meter which is intended to have an accuracy of the order of 0.1%.

Our investigations have shown that, at least in the case of a straight tube meter, the errors arise primarily due to changes in tension in the metering tube. It is known that frequency of vibration is dependent on tension in the tube (as well as fluid density) and it is known to take a single measurement of tension and store this. However as mentioned, the tension is liable to change, particularly with temperature fluctuations, and also with aging of the tube.

To enable tension measurements to be made in situ, it is known to mount one or more strain gauges on the flow meter tube and to obtain a measure of strain from the strain gauges. Pursuant to the invention it is has been appreciated that provision of strain gauges may not give accurate results, as they only provide a local indication of strain. The strain gauges may also require calibration and temperature compensation.

Changes in tension are generally less of a problem in meters which have a higher compliance, for example where the length of the metering tube is large in comparison to the distance between fixing points and incorporates one or more bends, an example being a B-tube meter. Nonetheless, other factors which may affect stress in the tube, for example pressure, may affect density measurements or other measurements such as flow.

EP-A-848234 and U.S. Pat. No. 5,734,112 both disclose coriolis flow meters having two parallel bent tubes with sensors mounted close to first and second nodes of vibration and wherein the tubes are excited in two modes of vibration.

EP-A-701 107 discloses an arrangement in which the resonant frequencies of two vibration modes of a straight tube meter are measured and in which it is demonstrated that the ratio of the two frequencies is a linear function of tension. Thus, from the ratio of frequencies, a measure of tension can be calculated. We have investigated the techniques and assumptions proposed in that disclosure, as discussed further below and have discovered that, whilst the reasoning and results presented in that disclosure are useful and may provide a useful improvement on previous strain-gauge methods, there is room for improvement and the technique cannot produce highly accurate meters. Specifically, analysis pursuant to the invention reveals that, surprisingly, the relationship is not truly linear, nor can it be readily corrected, and better results can be achieved by a different approach. FIG. 15 shows the error in the stress estimate based on a technique as disclosed.

In a general aspect, the invention proposes use of measurements of resonant frequencies for two or more independent vibrational modes of a metering tube to obtain a measure of density of fluid in the metering tube compensated for variation of stress in the metering tube or to obtain a measure of stress in the metering tube wherein the ratio of said resonant frequencies is dependent on density or wherein the stress is determined as a non-linear function of the ratio of said resonant frequencies.

In a first method aspect, the invention provides a method of obtaining a measure of stress in a fluid metering tube, the fluid having a density, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of stress from said first and second resonant frequencies based on modelling the fluid density as a first function of stress and the first resonant frequency and modelling the fluid density as a second function of stress and the second resonant frequency and solving to determine stress as a function of said frequencies.

In a second method aspect, the invention provides a method of obtaining a measure of stress in a fluid metering tube, the fluid having a density, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of stress from said first and second resonant frequencies based on determining possible pairs of values of stress and density corresponding to one of the first and second resonant frequency and selecting a pair of values based on the other of the first and second resonant frequencies.

In a third method aspect the invention provides a method of obtaining a measure of density of fluid in a metering tube, the tube being subjected to a stress, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of density from said first and second resonant frequencies based on modelling the fluid density as a first function of stress and the first resonant frequency and modelling the fluid density as a second function of stress and the second resonant frequency and solving to eliminate stress.

As will become apparent as the description proceeds, all of the above aspects stem from a common and novel approach to determination of density or stress in a metering tube which not only may provide better results than prior art techniques but may be simpler to implement. It will be apparent that the above techniques are not limited to implementations where the ratio of the two frequencies is independent of density; the methods may be used where the ratio of the first and second frequencies varies with density and/or where the stress is not a linear function of this ratio (whether or not this ratio is explicitly determined (unlike the prior art, there is no need to determine this ratio)). Whilst the invention works where such constraints are not met, it of course equally works if they are met; indeed such constraints are not directly relevant to the invention.

Preferred features are set out in the dependent claims and other preferable and optional features and the advantages thereof will be apparent from the following.

The invention extends to apparatus arranged to perform a method according to any method aspect, which may comprise a signal processor of a flowmeter and may include said metering tube.

In a first apparatus aspect, the invention provides apparatus for obtaining a measure of stress in a fluid metering tube, the fluid having a density, the apparatus comprising:

exciter means for inducing first and second vibration modes in the tube and obtaining a first resonant frequency of the first vibration mode which is a first function of stress and density;

frequency measurement means for obtaining a second resonant frequency of the second vibration mode which is a second function of stress and density; and processing means for deriving said measure of stress from said first and second resonant frequencies based on modelling the fluid density as a first function of stress and the first resonant frequency and modelling the fluid density as a second function of stress and the second resonant frequency and solving to determine stress as a function of said frequencies.

In a second apparatus aspect, the invention provides apparatus for obtaining a measure of stress in a fluid metering tube, the fluid having a density, the apparatus comprising:

exciter means for inducing first and second vibration modes in the tube and obtaining a first resonant frequency of the first vibration mode which is a first function of stress and density;

frequency measurement means for obtaining a second resonant frequency of the second vibration mode which is a second function of stress and density; and processing means for deriving said measure of stress from said first and second resonant frequencies based on determining possible pairs of values of stress and density corresponding to one of the first and second resonant frequency and selecting a pair of values based on the other of the first and second resonant frequencies.

In a third apparatus aspect, the invention provides apparatus for obtaining a measure of stress in a fluid metering tube, the fluid having a density, the apparatus comprising:

exciter means for inducing first and second vibration modes in the tube and obtaining a first resonant frequency of the first vibration mode which is a first function of stress and density;

frequency determining means for obtaining a second resonant frequency of the second vibration mode which is a second function of stress and density; and processing means for deriving said measure of stress from said first and second resonant frequencies based on determining possible pairs of values of stress and density corresponding to one of the first and second resonant frequency and selecting a pair of values based on the other of the first and second resonant frequencies.

The invention further provides a method of determining parameters, functions, look-up tables or coefficients for use in the preceding aspects and further provides look-up tables and the like so generated. In an exemplary aspect of this, the invention provides a method for use in determining a measure of stress or density comprising performing a method according to any preceding method aspect for a plurality of values of stress and density and determining an empirical function or look-up table of values relating said first and second resonant frequencies to stress or density. The method may further comprise storing said empirical function or look-up table in memory means.

The invention further provides a computer program or computer program product comprising instructions for performing any methods disclosed herein.

Although the invention is primarily concerned with methods and apparatus as set out above, it is a further general aim of the invention to provide an improved method of obtaining a measure of a variable, particularly stress, which is dependent on factors such as tension or pressure and indirectly dependent on temperature, in a flow meter tube which may affect measurement of a parameter such as density, or to provide an improved measure of density or other parameter which is less prone to errors due to changes in the variable. Further aspects and preferred features may achieve this, and may be applied to the preceding aspects, as will be set out below.

The invention may provide a method of obtaining a measure of a variable in a metering tube comprising inducing a first vibration mode in the tube and obtaining a first measure of at least one characteristic of the first vibration mode which is a first function of the variable; obtaining a second measure of at least one second characteristic which is a second function of the variable; and deriving said measure of the variable from said first and second measures. The variable is preferably related to stress in the tube and may be a measure of tension or pressure or of stress itself.

The measure of the variable may be output directly. For example, it may be useful to obtain a measure of pressure in the tube. Alternatively, the variable may be used to derive a more accurate measure of density or other desired parameters of fluid in the tube. The variable need not be explicitly determined, but instead a measure of density or other desired parameter which is substantially independent of the variable may be derived directly from the first and second measures.

Thus, in a further aspect, the invention may provide a method of obtaining a measure of a desired parameter of fluid, preferably density of fluid, in a metering tube, the method comprising inducing a first vibration mode in the tube and obtaining a first measure of at least one characteristic of the first vibration mode which is a first function of said desired parameter and a further variable; obtaining a second measure of at least one second characteristic which is a second function of at least said further variable; and deriving a compensated estimate of said desired parameter from said first and second measures which compensated estimate of the desired parameter is substantially independent of the variable. By substantially independent is meant that the compensated estimate preferably has less dependence on the further variable than an estimate based on the first measure alone, although some dependence may remain. The variable is preferably related to stress in the tube and may be a measure of tension or pressure or of stress itself.

In both the immediately preceding aspects, the variable is determined (in the first aspect) or compensated for (in the second aspect) based on a measure of the first characteristic which is directly derived from the vibration induced in the tube. This may offer advantages over conventional methods which rely on indirect methods such as using strain gauges as the measurement should be directly affected in a similar way to desired properties which are being measured.

Although the primary effect of stress in a straight tube meter is on the apparent measurement of density, there is also an effect on other parameters such as flow rate. Although the effect on flow rate is generally smaller (because the flow rate may depend on a ratio of two frequencies, so similar errors in both frequencies will tend to cancel), it may nonetheless be desirable to correct any such errors and this may be made possible if the stress is known.

Although the second characteristic could in principle be any physical characteristic affected by the first variable (preferably stress-related), for example speed of sound or electrical conductivity, preferably said at least one second characteristic is at least one characteristic of a second vibration mode induced in the tube. The first vibration mode is preferably us ed to determine fluid flow characteristics, particularly density from the resonant frequency. By using one or more characteristics of a second vibration mode, the effects of other factors which tend to affect both measurements similarly may be minimised or cancelled and a more reliable determination of the overall effect of the second variable can be determined.

Preferably the first measure includes the resonant frequency of the first vibration mode and the second measure includes the resonant frequency of the second vibration mode. Both frequencies are functions of both the (stress-related) variable (primarily tension in a straight tube meter, primarily pressure in a thin-walled high compliance meter) in the tube and fluid density (and possibly other parameters). The measurements obtained may be combined to obtain a measure of density which is substantially independent of the tension in the tube. The measure of tension (or other variable) or density (or other parameter) may be derived from the measured resonant frequency according to a predetermined formula based on the dimensions and material of the tube, and optionally including a compensation factor to take into account the presence of fluid in the tube. Alternatively, the measure of tension (or other variable) or density (or other parameter) may be obtained from an empirically stored relationship between measured frequency and tension. This relationship may be derived by obtaining measurements from the tube, or from a similar tube during an initial calibration step.

The first and second vibration modes are preferably substantially orthogonal. The modes may be spatially oriented in substantially orthogonal respective first and second spatial directions, for example along respective x and y axes of the tube. Alternatively, one mode may be a longitudinal bending mode and the other mode may be a torsional vibrational mode. The tube may be selected or mounted to have different vibrational properties in said first and second spatial directions. For example, rather than a cylindrical tube, the tube may be asymmetric, preferably having a rectangular or oval cross-section; this will give a greater bending stiffness in the wider cross-sectional direction. Additionally or alternatively, the tube may be mounted to enhance or decrease bending stiffness in one of said spatial directions, for example by fixing on two opposite sides, but not around the whole perimeter of the tube; this will give greater bending stiffness in a plane passing through the fixing points (the use of an asymmetric tube to induce bending preferentially in one direction is known, but it has not been proposed to excite such a tube independently in two directions for the reasons outlined above). This may be used to enhance separation of vibration frequencies. Furthermore, by using spatially perpendicular modes, the sensors and actuators may be designed to couple primarily to the desired spatial mode and to be relatively poorly coupled to the other mode, thereby facilitating separation of signals and driving. Alternatively the modes may be orthogonal by virtue of frequency but be spatially coincident; this reduces the number of physical sensors required. Both modes may be longitudinal modes. The modes will normally have different resonant frequencies but this is not necessary. It is desirable, however, that the frequencies of the modes chosen are different functions of stress and density, for example that the variation with or partial derivative with respect to each of stress and density has a different value.

Surprisingly, we have found that measurement of a torsional vibrational resonant frequency may provide a convenient yet effective and reliable means for determining or compensating for tension within the tube, and may not be adversely affected by temperature; measurement of a torsional resonant frequency may be provided independently. A further advantage is that it may be possible to detect the vibration using the sensors, or modified sensors, used to detect the main (bending vibration mode) used to detect flow. Surprisingly, the torsional resonant frequency is normally largely unaffected by the flow of fluid in the tube, although it has been found that the viscosity of the fluid may affect the measurement. However, in many configurations, the torsional resonant frequency is only slightly dependent on stress. The method may include signalling a fault based on the measured value of the variable or based on the torsional resonant frequency. In particular, in the event of two values of the characteristic giving implausible values for stress or density, this may be used to signify a calibration drift or other possible fault. More preferably, three or more independent parameters, for example two vibration characteristics and an independent stress or temperature measurement, or three vibration characteristics may be compared to determine a measure of accuracy or to identify a potential fault.

The invention extends to apparatus for implementing any of the above method aspects.

An embodiment of the invention will now be described, by way of example, with reference to the accompanying drawings in which.

Figure 5:
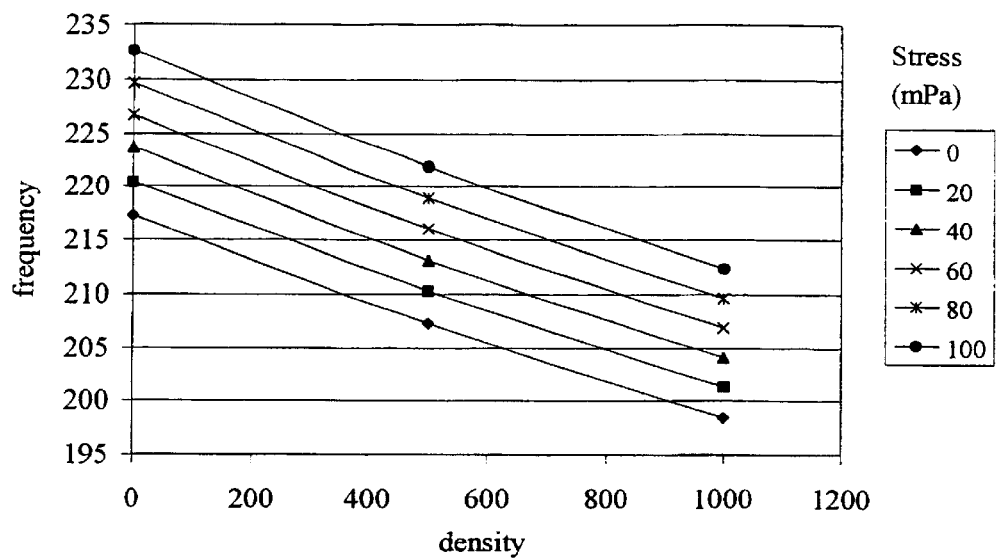
FIG. 5 shows how the frequency changes with density with axial stress as a parameter.
Figure 6:
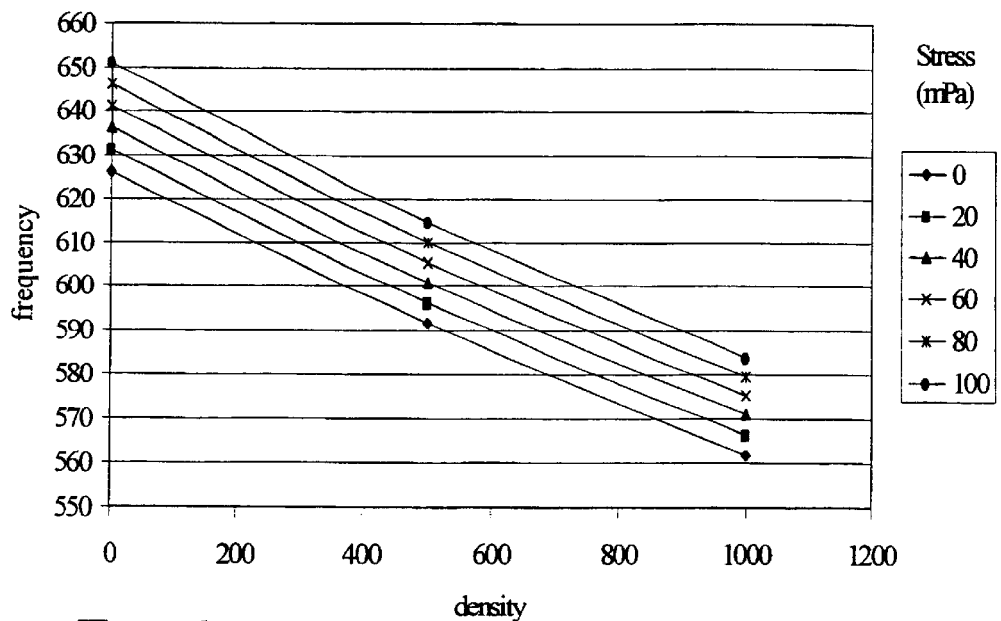
FIG. 6 shows the mode 2 frequency for the same sensor as FIG. 5.
Figure 7:
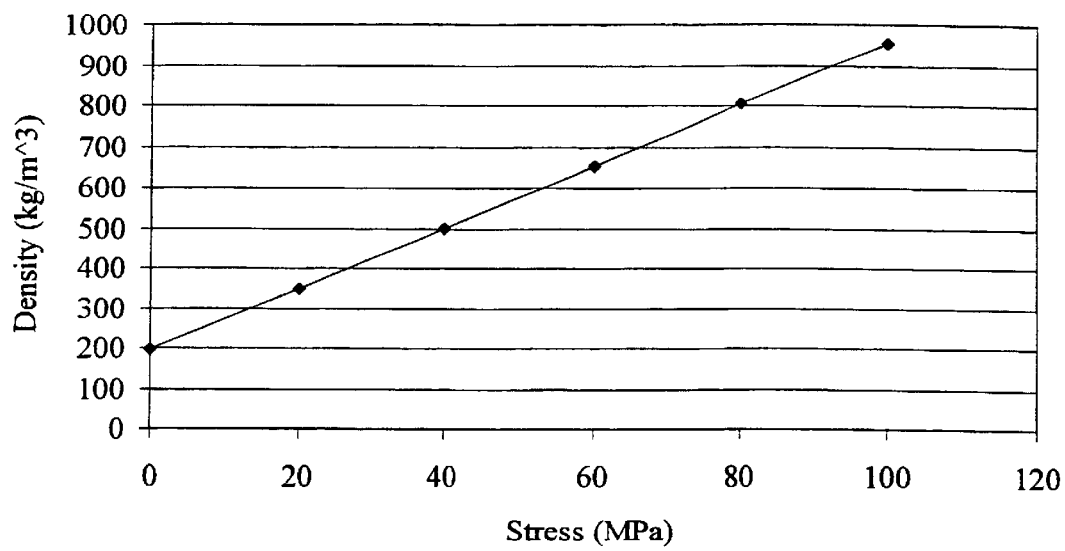
FIG. 7 shows the locus of stress, density pairs which correspond to the first frequency.
Figure 10:
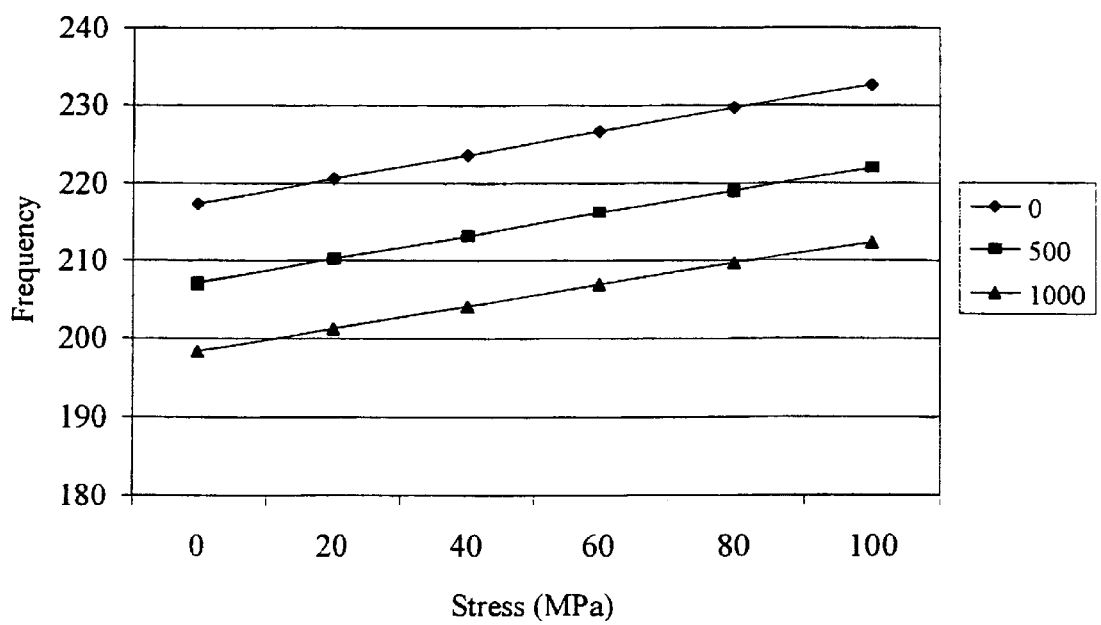
Figure 11:
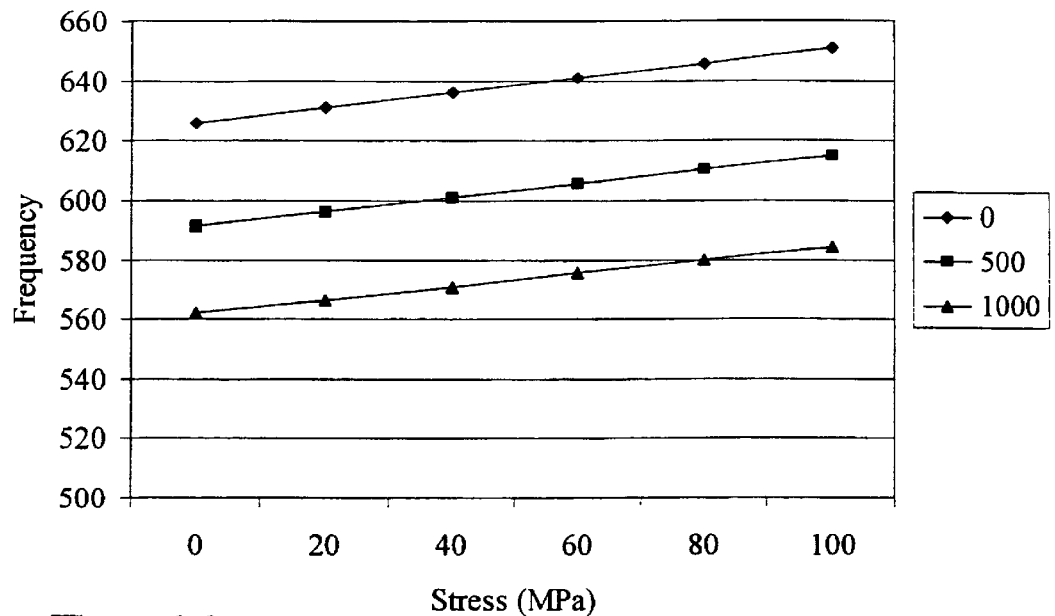
Figure 12:
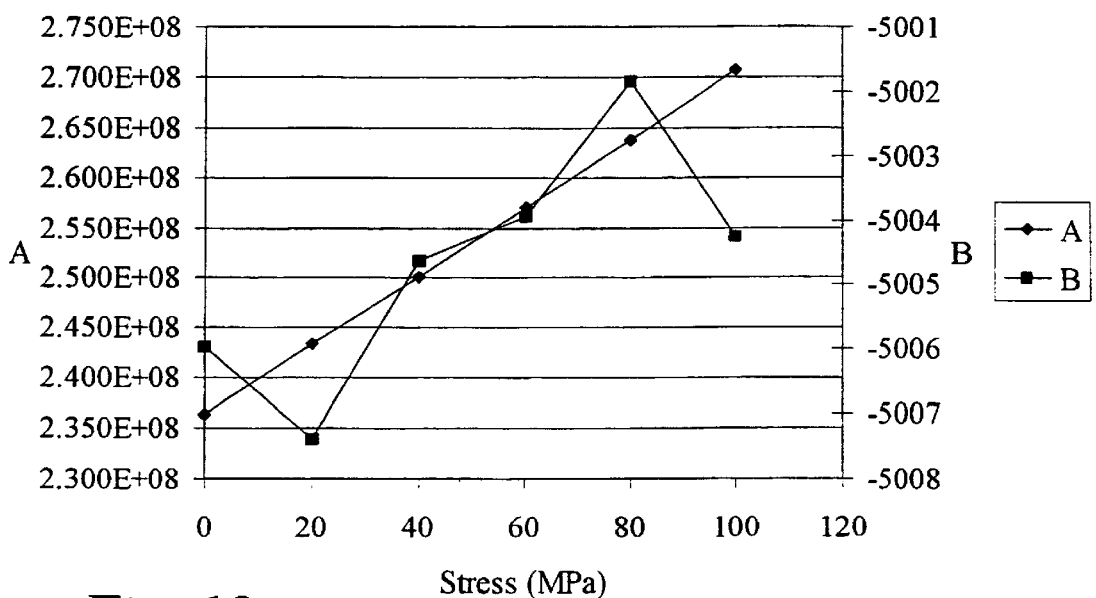
Figure 13:
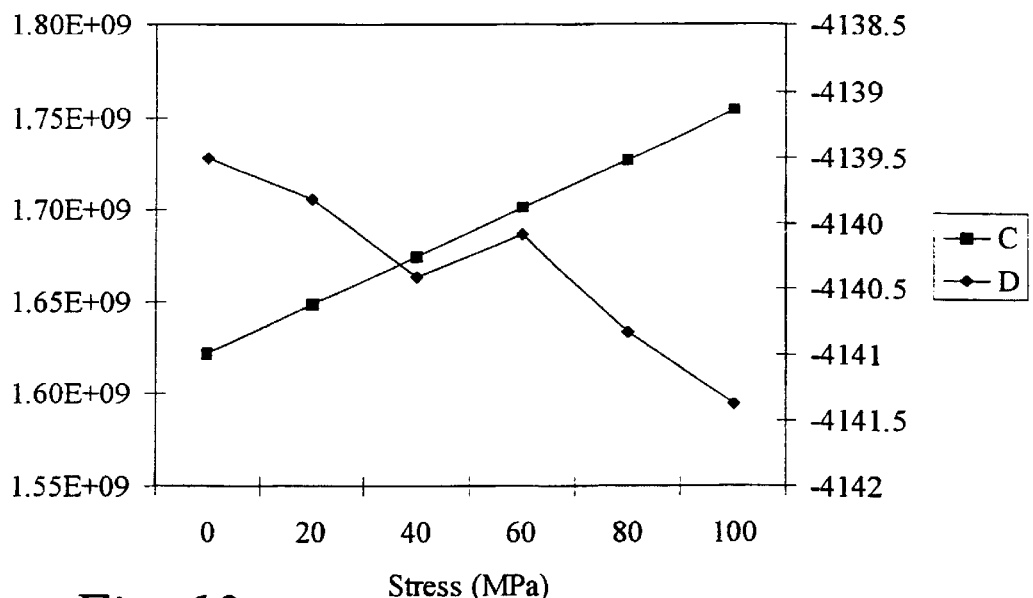
Figure 14:
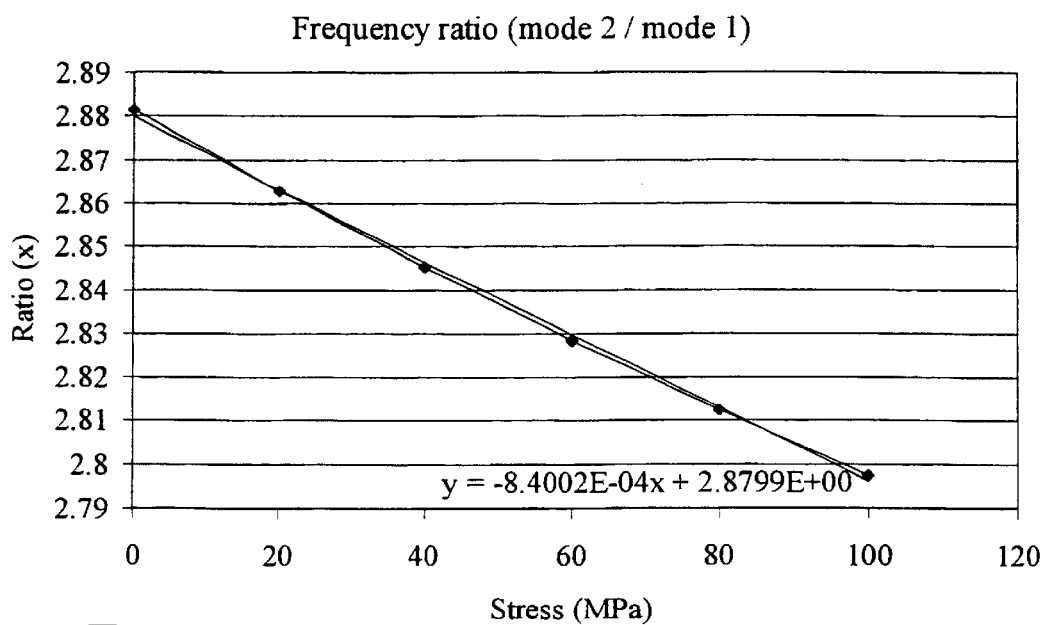
Figure 15:
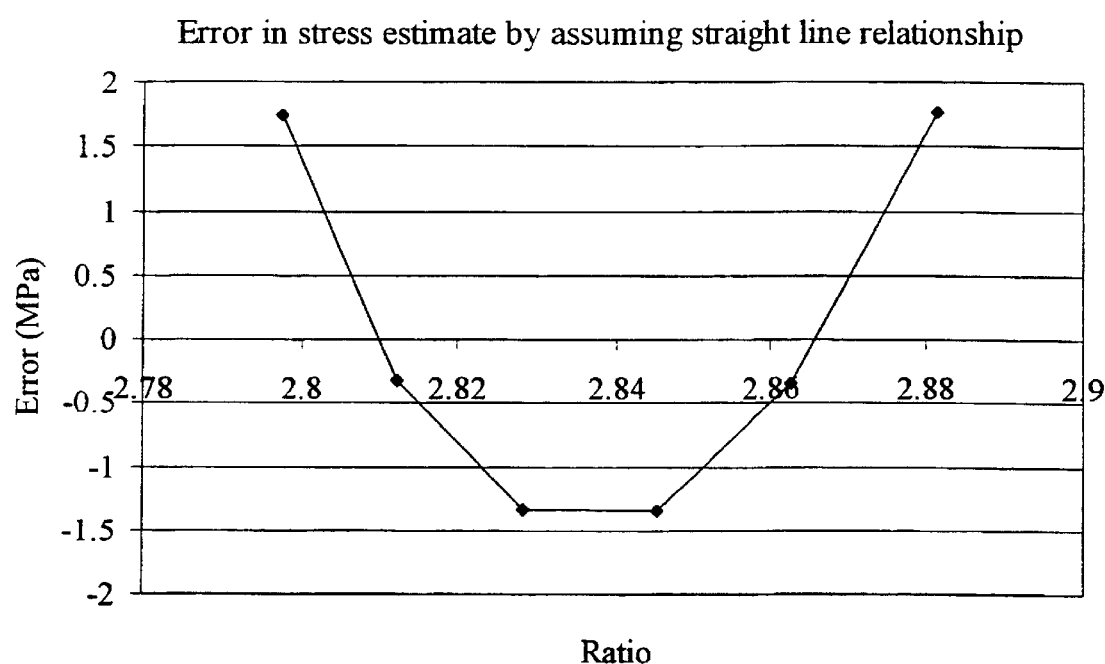

FIGS. 10 and 11 show respectively mode 1 and mode 2 resonant frequency against stress with density as a parameter;

FIG. 12 shows a graph of A and B of equation (1) as a function of stress;

FIG. 13 shows C and D of equation (2) as a function of stress;

FIG. 14 shows the frequency ratio derived from the data of FIGS. 5 and 6; and FIG. 15 shows the error of prior art technique as a function of the measured frequency ratio.

By way of introduction, some important considerations underlying the embodiment will be discussed.

The emphasis of this description is on making an accurate density measurement, independent of the stress within the measuring tubes. However, the technique does also determine the stress levels within the tube. Therefore, since this stress may affect the flow sensitivity of the meter, the stress determined in this invention may be used to compensate for flow factor changes with stress.

There are essentially two categories of meter to which the invention may be applied.

Category 1: Low Stress.

The designs of these category sensors typically have:
  Measuring tubes which have bends of at least 180 degrees, ie some sort of loop
  Distance between the ends of the measuring section short compared to the active length of the measuring section
  Measuring tubes are mounted from a structure which is in good thermal contact with the process fluid The significance of these features is that:
  Axial loads create insignificant stress in the measuring tubes
  Changing process temperatures cause no significant stress in the measuring tubes
  The only temperature that affects the stress in the tubes is the process temperature
  Temperature only affects frequency through the material stiffness changing with temperature (small effect) and the geometry changing with temperature (small)
  These two effects are additive, small and only dependent on process temperature
  Because the effect is small and only dependent on process temperature, it is very easily compensated for However, pressure may affect stress to a noticeable degree.

Category 2: Stressed

The designs of these category sensors typically have:
  Relatively straight (no loops) or straight measuring tubes
  Distance between ends of measuring tubes 50% or more of the active length
  Measuring tubes mounted on a support (either internal beam structure or the case is structural) which is not in good thermal contact with the process fluid The significance of these features is that:
  Axial loads may cause stress in the measuring tubes
  Changing process temperatures cause stress in the measuring tubes, particularly while there is significant temperature difference between the measuring tubes and the support structure
  Even ambient temperature may change the stress in the measuring tubes in as much as it may change the temperature of the support structure (particularly if the support structure is the case)
  The stress in the tubes is not a simple function of the process temperature
  The stress in the tubes depends on process temperature, ambient temperature and time (thermal lag)
  Temperature affects frequency through the material stiffness (small), change in geometry (small), stress developed by relative temperature of measuring tubes and support structure (large)
  Because the stress effects are large and not simply dependent on the process temperature, the effects are not easily compensated The theory underlying the invention will now be described.

Theoretical Analysis

For transverse modes of vibration, the frequency of each mode can be described by the following equation:

$$freq = \frac{1}{2\pi}\sqrt{\frac{k}{m_2 + m_d}} \qquad (1)$$

where k is the effective stiffness for a given mode, $m_t$ is the effective mass of the tube (for the given mode) and $m_d$ is the effective mass of the fluid (for the given mode).

We have stressed 'for the given mode' because all of these numbers will change for different modes. In particular, the $m_d$ will always be directly proportional to density, but the constant of proportionality will generally be different for each mode.

Because the term k/m is a ratio, it is not easy to determine the individual parameters. However, re-arranging (1) and knowing $m_d$ is directly proportional to density, we get $$density = A + \frac{B}{freq^2} \qquad (2)$$

There are pairs of A,B for each transverse mode. A and B are generally functions of stress, which in a straight meter is strongly dependent on temperature, (B much more so than A)

The technique is described with reference to mode 1 and mode 2. These could conveniently be the first two transverse modes in the same plane (ie not the same mode in two different planes). Equally, a pair of modes for which (2) holds could be used. Particularly advantageous is the possibility of designing the sensor with this invention in mind, in which, case it is possible to design modes which will not interfere with the Coriolis measurement but will enhance the density measurement by this technique. Examples of this are designing for orthogonal modes of vibration, discussed later.

Given any two different (sufficiently different to have different frequencies) modes that satisfy eqn (2), designated modes 1 and 2, the following equations can be seen to apply:

$$density = A + \frac{B}{f_1^2} \qquad (3)$$

$$density = C + \frac{D}{f_2^2} \qquad (4)$$

These equations apply at a given operating point (of stress and temperature) for mapping density to frequency.

For category 1 (stress free) sensor geometries, A and C are essentially constant, while B and D have a small temperature dependence. This arises from the stiffness of the material used in the measuring tubes reducing slightly with increasing temperature.

For category 2 (stressed) designs, B and D may be strongly dependent on the stress in the tubes.

For a single straight-tube meter, these problems are severe. The change in frequency due to temperature effects is of the same order of magnitude as the change with density. However, the practicalities of mounting a strain gauge, reading the gauge accurately, inferring stress from the strain reading, correcting for the large stress effects all mean that this compensation is far from perfect and is inelegant.

Let s be the longitudinal stress in the measuring tube. It is assumed to be uniform for simplicity. This assumption is valid for a uniform tube constrained only at its ends.

Theoretical analysis (backed by Finite Element Analysis) suggests that A is essentially independent of stress s, while B is a non-linear function of stress s. Likewise for C and D. For generality, each parameter is assumed to be a $2^{nd}$ order polynomial function of s. This was certainly case for the author's model. The general method being described does not depend on the nature of this function, just that it is known, either by theory, modelling or experiment.

Therefore, eqns (3) and (4) become $$density = A_0 + A_1 s + A_2 s^2 + \frac{B_0 + B_1 s + B_2 s^2}{f_1^2} \quad (5)$$

$$density = C_0 + C_1 s + C_2 s^2 + \frac{D_0 + D_1 s + D_2 s^2}{f_2^2} \quad (6)$$

Since density and s are equal for both equations, it is possible to equate equations 5 and 6. Equating and collecting terms, we get equation 7:

$$\left\{ A_0 - C_0 + \frac{B_0}{f_1^2} - \frac{D_0}{f_2^2} \right\} + \left\{ A_1 - C_1 + \frac{B_1}{f_1^2} - \frac{D_1}{f_2^2} \right\} s + \left\{ A_2 - C_2 + \frac{B_2}{f_1^2} - \frac{D_2}{f_2^2} \right\} s^2 = 0$$

This is a quadratic equation in s and has two solutions. It is a simple matter to determine the appropriate root. This gives a value for s, the stress. This value can now be substituted into either (5) or (6) (as they are equal) and a value for density can be derived.

The mathematics shown can be modified according to the relationship between A, B, C and D and the stress s. For example, some of the coefficients above may be zero as mentioned earlier. Or, the relationship may be higher than a $2^{nd}$ order polynomial as used here. In such cases, a closed form solution for s might not exist. In this case, the function might be approximated by a $2^{nd}$ order polynomial as here, or as a different function which would give a closed form solution. If no closed form solution exists, then s might be evaluated iteratively by any number of numerical methods.

The above model gave very accurate answers using the equations above.

As will have been appreciated by now, the method amounts to solving two simultaneous linear equations. As will also be appreciated, this can be understood in terms of finding the unique point on a graph where two straight lines cross.

When these considerations are applied to this method, it will be appreciated that the uncertainty in determining s depends, among other things, on the difference in slope between the two lines. For the above model, the difference in slopes was a factor of at least 2, giving good resolution of the interception point.

Measuring Torsional Vibration

Figure 1:
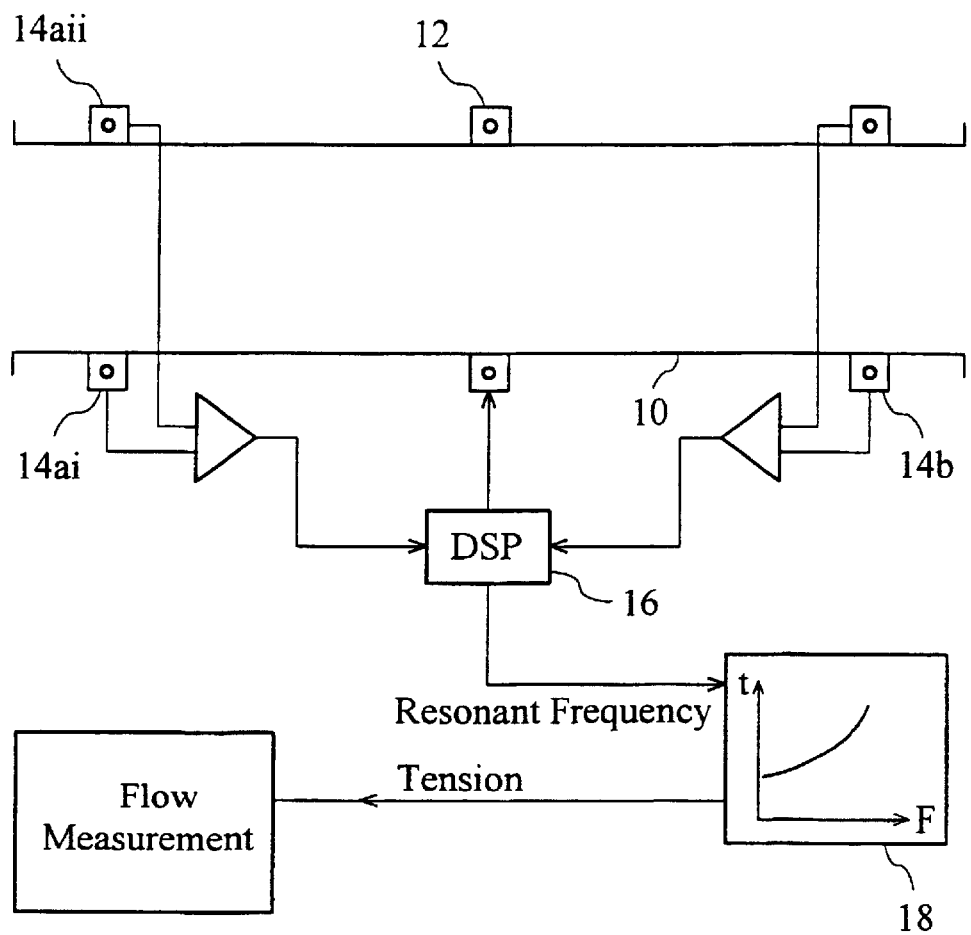
FIG. 1 is a schematic diagram of a flow meter in which torsional resonant frequency can be measured.

Although two longitudinal modes may be used, it may be desirable to measure torsional vibrations, and this possibility will be briefly discussed, before discussing some worked examples. Referring to FIG. 1, an embodiment comprises a straight Coriolis metering tube 10. The invention may be applied to other tube configurations, but is most preferably applied to straight tubes, where the introduction of torsional vibrations causes minimal interaction with other vibrational modes. The ends of the tube are rigidly clamped and a driver 12 for inducing torsional vibration is mounted near the centre of the tube. Alternatively, a pair of drivers for inducing torsional vibration may be mounted spaced apart on the tube 10. These drivers may comprise, for example, electromagnetic transducers similar to the transducers for inducing other vibrational modes. A torsional displacement sensor 14a is mounted towards one end of the tube and another sensor 14b is mounted at a spaced apart location, typically towards the other end of the tube. Both sensors are arranged to detect torsional vibration. Sensor 14a comprises a pair of diametrically opposed partial sensors 14ai, 14aii comprising a relatively movable coil and magnet, one of which is mounted on the tube and the other of which is fixed. The outputs of the pair of partial sensors are combined to produce the sensor output; this arrangement gives a balanced sensor and a less noisy output signal.

The outputs of the sensors 14a, 14b are passed to a digital signal processor 16, incorporating a feedback amplifier, which controls the driver 12. The signal processor 16 is arranged to drive the torsional driver 12 to induce torsional resonance, based on feedback signal from the sensors 14a, 14b, and also to measure the resonant frequency.

It is also possible to obtain other information, for example the condition of the tube or a measure of the viscosity of fluid in the tube from the amplitude of the signal from the sensors compared to the driver signal. It may also be possible to detect a fault such as a crack in the tube and to signal an alarm.

Figure 2:
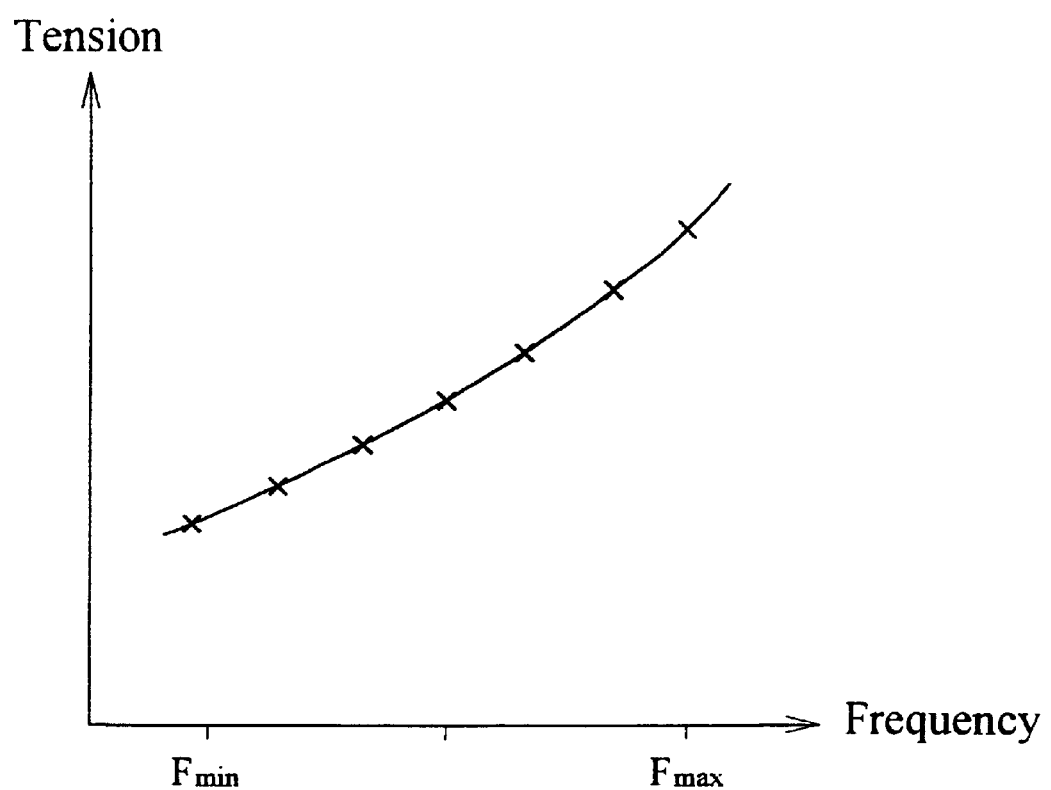
FIG. 2 is a graph showing the empirical relationship between tension in the tube and measured frequency.

Once stable oscillation is induced, the processor 16 determines a measure of tension within the tube by reference to a look up table 18 in which is stored a calibration curve similar to the empirical calibration curve depicted in FIG. 2. The calibration curve may be stored by specific calibration of the meter in question or may be a generic curve for a particular class of meter.

The measure of tension so determined is output for use in measurement of flow and other parameters.

For the sake of clarity, the components used to determine flow have not been shown in FIG. 1. These will normally include a driver to induce bending mode vibrations and a pair of sensors to detect the bending vibration and the phase of vibration at spaced apart locations on the tube. There will also be associated control electronics for inducing resonant oscillation. In a preferred arrangement some or all of the flow measurement components may be integrated with the components used to measure tension. In particular, the processor 16 may control both torsional and vibrational modes. Indeed, it is desirable if these functions are linked, as the processor 16 is then able to "know" exactly what excitation is applied to the tube. A measurement of torsional vibration may be obtained from the same sensors which are used to detect bending mode vibrations, if those sensors are appropriately configured. The look up table will normally be stored in the DSP.

Worked Examples

Two examples will be given of the calculation of tension and density for a straight tube meter.

Example 1 uses longitudinal modes 1 and 2
Example 2 uses longitudinal modes 1 and 3

Similar principles apply if one (or both) modes is a torsional mode, although the numbers may of course be different.

In the first stage, data is collected for the two modal frequencies as a function of density and stress.

This could be done totally experimentally or finite element analysis could be used to determine general characteristics which could then be 'calibrated' by a few experimental points.

A good method is to start with air in the meter and then ramp the temperature of the meter to create various stresses, and then to repeat with water in.

For this technique, the data should ideally be measured for 2 or more densities at 3 or more stress levels. The stress needs to be constant for each set of densities. If it is not possible to get a 'regular' array such as this, then it is generally necessary to fit the data in some way and then interpolate to get regular data.

The measured data for each of modes 1,2 and 3 for a given straight tube meter are shown in tabular form below.

|        |       | density |        |
|--------|-------|---------|--------|
| stress | 0     | 500     | 1000   |
| Mode 1:- |     |         |        |
| 0      | 255.31 | 219.88 | 196.01 |
| 20     | 261.89 | 225.55 | 201.07 |
| 40     | 268.29 | 231.06 | 205.99 |
| 60     | 274.53 | 236.43 | 210.77 |
| 80     | 280.62 | 241.67 | 215.45 |
| 100    | 286.56 | 246.79 | 220.01 |
| Mode 2:- |     |         |        |
| 0      | 699.13 | 602.17 | 536.85 |
| 20     | 708.15 | 609.94 | 543.78 |
| 40     | 717.05 | 617.61 | 550.62 |
| 60     | 725.84 | 625.17 | 557.36 |
| 80     | 734.51 | 632.64 | 564.02 |
| 100    | 743.07 | 640.02 | 570.59 |
| Mode 3:- |     |         |        |
| 0      | 1355.6 | 1167.2 | 1040.3 |
| 20     | 1365.7 | 1175.8 | 1048   |
| 40     | 1375.6 | 1184.4 | 1055.7 |
| 60     | 1385.6 | 1192.9 | 1063.3 |
| 80     | 1395.4 | 1201.4 | 1070.8 |
| 100    | 1405.1 | 1209.8 | 1078.3 |

Figure 3:
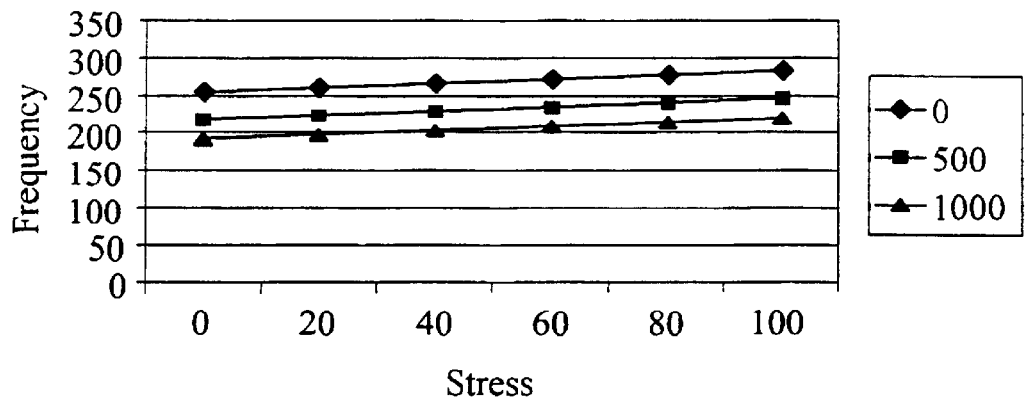
FIG. 3 shows frequency as a function of stress and density for each mode.
Figure 3:
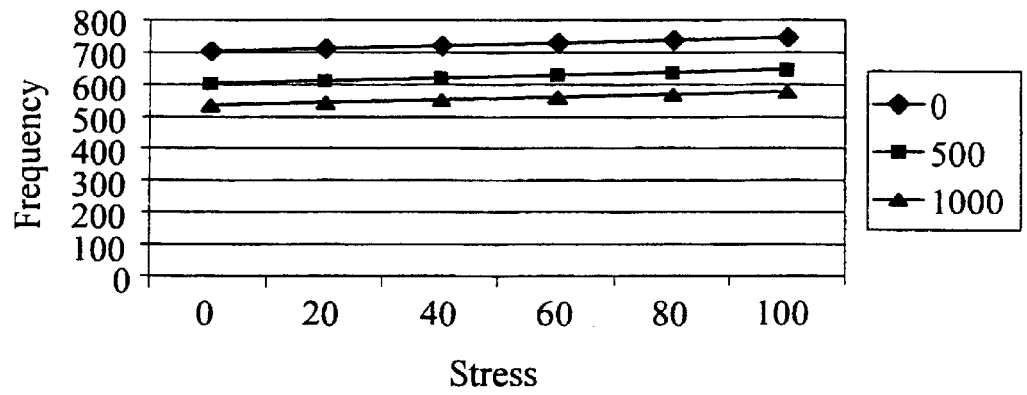
Figure 3:
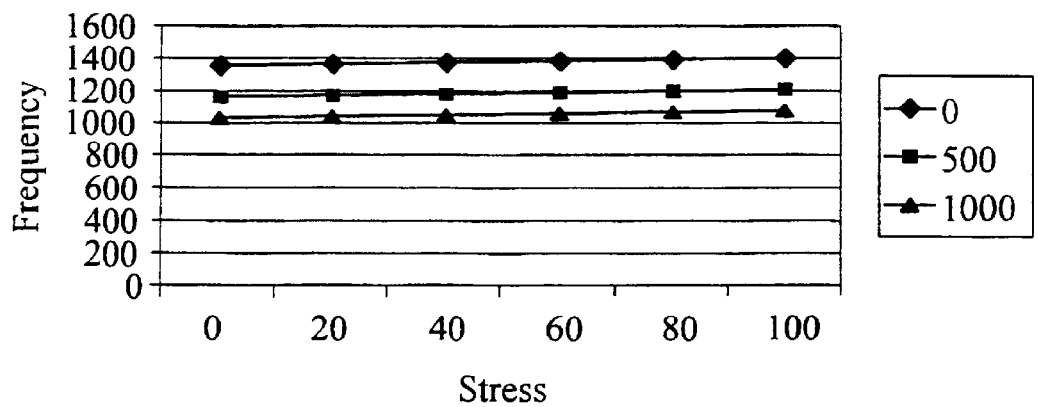

These data are plotted in FIG. 3, from which it can be seen that the frequency is lower at higher densities and increases with stress for each mode.

In the second stage, for each stress value, a best straight line is calculated for density vs $1/f^2$.

Density against (1/freq squared) should be a straight line, const A, slope B. This slope and offset is calculated for each mode and for each stress level.

These parameters can then be plotted against stress and used in later calculations. This gives a table of slope and offset for various stresses, for each mode of vibration.

This gives the data shown overleaf.

|        |            | density    |            |            |          |
|--------|------------|------------|------------|------------|----------|
| stress | 0          | 500        | 1000       | slope      | offset   |
| Mode 1:- |          |            |            |            |          |
| 0      | 1.53414E−05 | 2.06837E−05 | 2.60282E−05 | 93573490.53  | −1435.51 |
| 20     | 1.45802E−05 | 1.96569E−05 | 2.47346E−05 | 98478743.88  | −1435.82 |
| 40     | 1.38928E−05 | 1.87305E−05 | 2.35672E−05 | 103366160.9  | −1436.07 |
| 60     | 1.32685E−05 | 1.78894E−05 | 2.25104E−05 | 108202827.9  | −1435.68 |
| 80     | 1.26988E−05 | 1.7122E−05  | 2.1543E−05  | 113067956.7  | −1435.87 |
| 100    | 1.21778E−05 | 1.64189E−05 | 2.06593E−05 | 117903976.2  | −1435.83 |
| Mode 2:- |          |            |            |            |          |
| 0      | 2.0459E−06  | 2.75779E−06 | 3.46972E−06 | 702336678.1 | −1436.91 |
| 20     | 1.99411E−06 | 2.68798E−06 | 3.38184E−06 | 720600199.5 | −1436.96 |
| 40     | 1.94492E−06 | 2.62163E−06 | 3.29834E−06 | 738864870.8 | −1437.03 |
| 60     | 1.8981E−06  | 2.55861E−06 | 3.21906E−06 | 757025808.4 | −1436.92 |
| 80     | 1.85355E−06 | 2.49854E−06 | 3.14348E−06 | 775235292.3 | −1436.94 |
| 100    | 1.81109E−06 | 2.44125E−06 | 3.07151E−06 | 793388767.1 | −1436.89 |
| Mode 3:- |          |            |            |            |          |
| 0      | 5.44173E−07 | 7.34023E−07 | 9.24023E−07 | 2632616726 | −1432.53 |
| 20     | 5.36154E−07 | 7.23324E−07 | 9.10495E−07 | 2671361600 | −1432.26 |
| 40     | 5.28464E−07 | 7.12858E−07 | 8.97261E−07 | 2711518595 | −1432.94 |
| 60     | 5.20864E−07 | 7.02736E−07 | 8.84481E−07 | 2750147599 | −1432.51 |
| 80     | 5.13573E−07 | 6.92827E−07 | 8.72134E−07 | 2788928306 | −1432.29 |
| 100    | 5.06507E−07 | 6.83239E−07 | 8.60044E−07 | 2828557080 | −1432.65 |

In the third stage, a 2nd order polynomial is used to fit each of the slopes and offsets to stress level. Since mode 1 frequency is A+B/(f1^2) and mode 2 freq is C+D/(f2^2), and each of A,B,C,D is being described as a 2nd order polynomial (ie 3 coefficients) there are 12 coefficients in all.

Applying this to the above data yields the data shown overleaf.

Now online, in the working meter, knowing f1 and f2, a,b and c (the coefficients of a quadratic ax^2+bx+c=0) are determined, as above, as numbers. These are plugged into the well known eqn for solving quadratics, and the first root gives the stress.

Knowing the stress, this can be substituted into the A and B (or C and D) to calculate the density.

| stress | slope | offset | x2 | x3 | x4 | xy |
|---|---|---|---|---|---|---|
| | 93573490.53 | −1435.513274 | 0 | 0 | 0 | 0 |
| | 298478743.88 | −1435.818207 | 400 | 8000 | 160000 | 1969574878 |
| | 403366160.9 | −1436.067925 | 1600 | 64000 | 2560000 | 4134646436 |
| | 608202827.9 | −1435.682783 | 3600 | 216000 | 12960000 | 6492169677 |
| | 803067956.7 | −1435.868293 | 6400 | 512000 | 40960000 | 9045436540 |
| | 1007903976.2 | −1435.826509 | 10000 | 1000000 | 100000000 | 11790397620 |
| sum x | 3604593156.2 | −8614.776991 | 22000 | 1800000 | 156640000 | 33432225150 |
| | | | 6 | 300 | 22000 | 634593156.2 |
| | | | 300 | 22000 | 1800000 | 33432225150 |
| | | | 22000 | 1800000 | 156640000 | 2.49698E+12 |

| stress | slope | offset | x2 | x3 | x4 | xy |
|---|---|---|---|---|---|---|
| | 702336678.1 | −1436.906338 | 0 | 0 | 0 | 0 |
| | 2006000199.5 | −1436.95744 | 400 | 8000 | 160000 | 14412003990 |
| | 408864870.8 | −1437.030719 | 1600 | 64000 | 2560000 | 29554594833 |
| | 667025808.4 | −1436.915918 | 3600 | 216000 | 12960000 | 45421548505 |
| | 805235292.3 | −1436.944897 | 6400 | 512000 | 40960000 | 62018823386 |
| | 1093388767.1 | −1436.887849 | 10000 | 1000000 | 100000000 | 79338876715 |
| sum x | 4087451616 | −8621.643161 | 22000 | 1800000 | 156640000 | 2.30746E+11 |
| | | | 6 | 300 | 22000 | 4487451616 |
| | | | 300 | 22000 | 1800000 | 2.30746E+11 |
| | | | 22000 | 1800000 | 156640000 | 1.70911E+13 |
| | | | | Matrix of sums of x | | sumxy for mode 1 |

| stress | | x2y | xy | x2y | | |
|---|---|---|---|---|---|---|
| | 0 | 0 | 0 | 0 | | |
| | 20 | 39391497554 | −28716.36413 | −574327.2827 | | |
| | 40 | 1.65386E+11 | −57442.71698 | −2297708.679 | | |
| | 60 | 3.8953E+11 | −86140.96699 | −5168458.019 | | |
| | 80 | 7.23635E+11 | −114869.4635 | −91859557.077 | | |
| | 100 | 1.17904E+12 | −143582.6509 | −14358265.09 | | |
| sum x | 300 | 2.49698E+12 | −430752.1625 | −31588316.15 | | |
| | | −8614.776991 | 93578418.71 | −1435.582596 | B0 | A0 |
| | | −430752.1625 | 245167.3089 | −0.010787622 | B1 | A1 |
| | | −31588316.15 | −19.43403257 | 8.88577E−05 | B2 | A2 |

| stress | | x2y | xy | x2y | | |
|---|---|---|---|---|---|---|
| | 0 | 0 | 0 | 0 | | |
| | 20 | 2.8824E+11 | −28739.14881 | −5747882.9762 | | |
| | 40 | 1.18218E+12 | −57481.22876 | −2299249.15 | | |
| | 60 | 2.72529E+12 | −86214.95505 | −5172897.303 | | |
| | 80 | 4.96151E+12 | −114955.5918 | −9196447.342 | | |
| | 100 | 7.93389E+12 | −143688.7849 | −14368878.49 | | |
| sum x | 300 | 1.70911E+13 | −431079.7093 | −31612255.26 | | |
| | | −8621.643161 | 702339377.9 | −1436.915283 | D0 | C0 |
| | | −431079.7093 | 913908.5457 | −0.0028553 | D1 | C1 |
| | | −31612255.26 | −34.41886618 | 3.20512E−05 | D2 | C2 |
| | | sumxy for mode 2 | coeffs mode 1 | coeffs mode 2 | | | for modes 1 and 2. A similar set of calculations can be performed with the data for modes 1 and 3, or indeed any pair of modes.

In the final stage, the results are applied to give a plot of frequency as a function of density and stress and thence to enable both density and frequency to be determined in a working meter.

In a practical implementation, the preceding calculations will have been done offline, during calibration by the manufacturer and appropriate tables will have been stored in memory.

Figure 4:
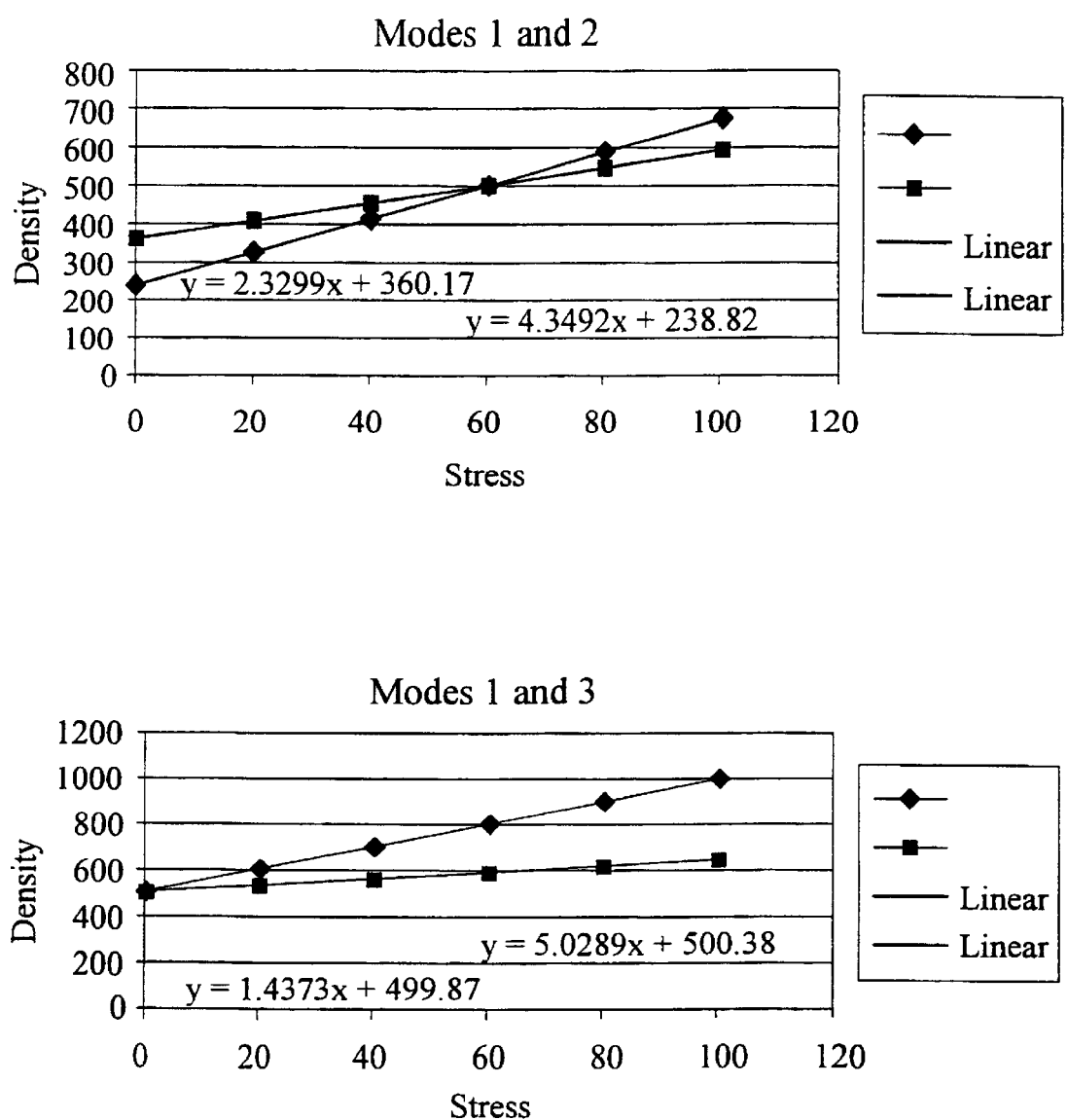
FIG. 4 depicts a solution for stress and density at the intersection of graphs of loci of possible pairs obtained from each mode.

FIG. 4 depicts this working.

The mode 1 frequency depends on two variables, density and stress. If the frequency is known, then for every possible stress there exists one density which would give that frequency. So line 1 (diamonds) on the upper graph of 1 shows every combination of density and stress which gives a particular measured frequency f1 (here 236.43). Likewise, line 2 shows every combination which gives the other measured frequency f2 (here 625.17). Because the stress and the density must be the same for the two modes, where these lines cross identifies the stress and the density, here a stress of 60 and a density of 500.

The lower graph of FIG. 4 shows a calculation using the data for modes 1 and 3 with a stress of 0 and a density of 500.

To obtain accurate results, it is desirable for the slopes of the graphs for each of the two modes used to differ as much as possible. More than two modes may be used as a further check, or to identify faults. The precise modes used may be chosen to suit a particular meter.

The above example provides a measure of both density and stress; if stress is not required, the equations may be solved to give a value of density alone.

A further worked example, explanation and comparison with the prior art will be given, with reference to FIGS. 5 to 15.

To recap, Coriolis meters utilise the fact that frequency is a function of density to determine density of media in addition to mass flow rate. However, in the straight meter, the frequency is also dependent upon the axial tension which is itself a function (primarily) of temperature distribution through the meter and to a lesser extent, pressure, external loading etc. As can be seen, the change in frequency due to stress is the same magnitude as the change due to a density change corresponding to air and water. Given just a measurement of frequency, it is not possible to determine density as the stress is unknown.

FIG. 5 shows how the frequency changes with density with axial stress as a parameter (the range shown is typical of a process meter).

FIG. 6 shows the mode 2 frequency for the same sensor as FIG. 5.

For completeness, it is noted that for ease of generating accurate data, and to avoid the risk that the technique is dependent on an artifact of meter construction, these data have been simulated using finite element analysis; it will be appreciated that to obtain a volume of data of the accuracy required to reveal possible shortcomings of the technique which are not attributable to experimental error is time consuming. However, by comparison of individual data with experimental data, the accuracy of the simulation has been verified and found to be consistent with measurements taken from a practical meter. Moreover, the results obtained are found in practice to apply to practical meters.

With the raw data plotted in FIGS. 5 and 6, it is not apparent how a solution to the problem may be found, so this will be explained again, with reference to the subsequent figures.

As stated, FIGS. 5 and 6 each show frequency of a given mode as a function of stress and density. For a given meter resonating under normal operation, it is possible to determine two modal frequencies, for example mode 1 and mode 2, but other modes may be chosen. It is also known that the density and stress values are the same for both modes—these are physical parameters of the tube.

Taking just the mode 1 frequency, there is one known quantity (frequency) and two unknowns (stress and density) so we cannot solve for the unknowns. It is, however, possible to determine a continuum of pairs of stress and density which give the same frequency as the measured mode 1. This is shown as a locus graph in FIG. 7 in which all points on the graph of stress vs. density have the same mode 1 frequency.

For the sensor that this data represents, a stress of 40 MPa and a density of 500 Kg/m^3 (it can be clearly seen that the point 40 MPa, 500 Kg/m^3 is on the locus—the actual values) gives a frequency of 213.14 Hz (the actual frequency). There is also a continuum of other possible pairs of density and stress which could give rise to the same frequency. For example, with zero stress, a density of 200 Kg/m^3 would give the same frequency.

Figure 8:
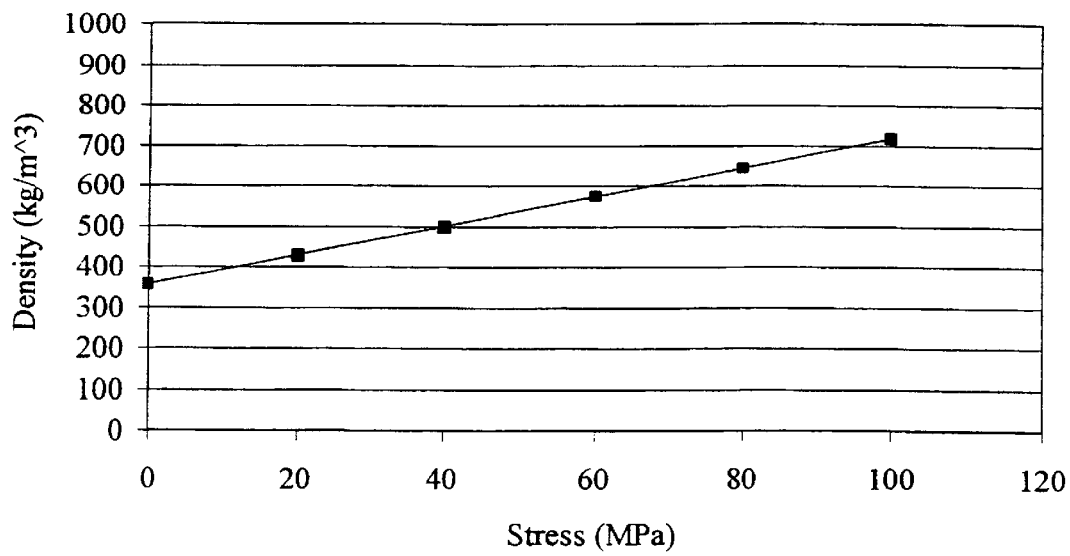
FIG. 8 shows the locus of stress, density pairs which correspond to the second frequency.

Likewise, for the sensor that this data represents, a stress of 40 MPa and a density of 500 Kg/m^3 gives a mode 2 frequency of 600.79 Hz (the actual frequency). Again, there is a continuum of other pairs of density and stress which could give rise to the same frequency for mode 2. This locus is shown in FIG. 8; again, it can be clearly seen that the point 40 MPa, 500 Kg/m^3 is on the locus.

Figure 9:
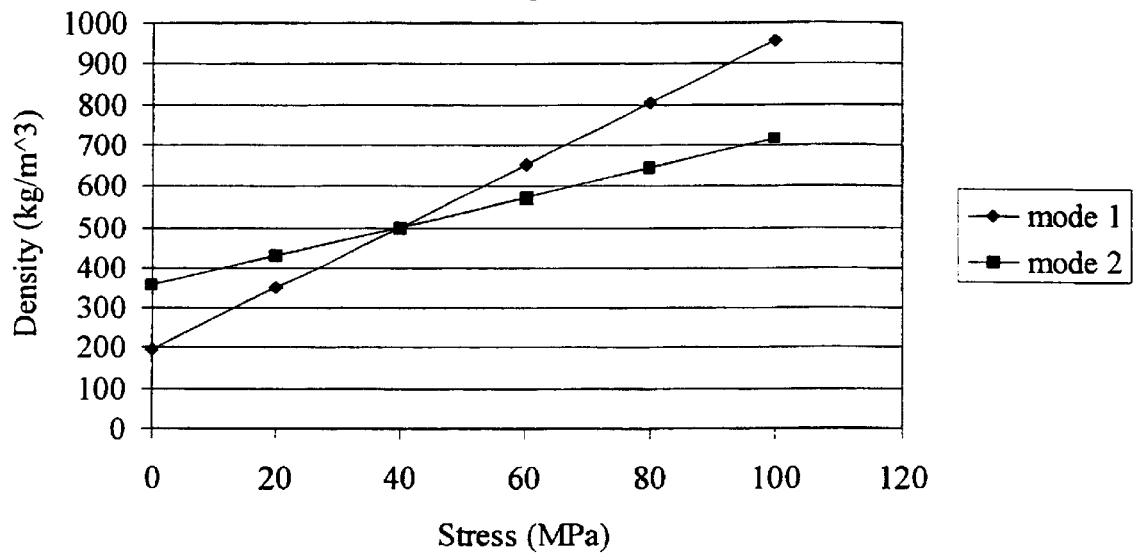
FIG. 9 shows the loci of FIGS. 7 and 8 superimposed.

FIG. 9 shows these two loci superimposed, specifically FIG. 9 shows the locus of stress, density pairs which give a mode 1 frequency of 213.14 Hz and the locus of stress, density pairs which give a mode 2 frequency of 600.79 Hz.

Because we know that the (stress, density) pair is the same for both modes because the frequencies were measured at the same time, the point where both loci predict the same (stress, density) pair must be the actual (stress, density) pair at the time the frequencies were measured. On FIG. 9, this point is the point where the lines intersect.

This is analogous to having two simultaneous equations and two unknowns, a solution is therefore possible. Although not evident from FIGS. 7 to 9, the loci are actually quadratic curves so there is a further root or point of intersection of no physical significance. In a practical implementation, this further root can be disregarded simply by rejecting the root which is not within a predetermined "sensible" range (the value is normally an order of magnitude at least away from a reasonable value so this does not require a the limits of the range to be carefully chosen.

The technique will now be explained in more detail.

The starting point is to obtain data about the two modal frequencies as a function of stress and density. For the purpose of this explanation, as noted above, the data has been obtained by finite element analysis. The finite element analysis model is used in practice so that the form of the equations is known and the data can be collected with a minimum of experimental points.

FIGS. 10 and 11 show respectively mode 1 and mode 2 resonant frequency against stress with density as a parameter.

Knowing that at a fixed stress and for a given mode, density and frequency are related by:

$$\text{Density} = A * (\text{freq}_{mode\ 1})^{-2} + B \qquad \text{Equation (1)}$$

Where A and B are constant for the given mode and stress condition, we can determine A and B for each value of stress.

To avoid confusion, we designate the 'A' and 'B' for mode 2 as C and D respectively. So for mode 2:

$$\text{Density} = C * (\text{freq}_{mode\ 2})^{-2} + D \qquad \text{Equation (2)}$$

FIG. 12 shows a graph of A and B as a function of stress. B is essentially independent of stress (as theory would predict) while A is strongly dependent on stress.

FIG. 13 shows C and D as a function of stress.

Note in both FIGS. 12 and 13 that the right hand abscissa, which shows B and D respectively varies over a range of only a few parts per thousand, thus the apparent random fluctuations in B and D are only of the order of 0.1% and can be discounted. The left hand abscissa, however, varies over a range of about 20% so the apparent near-linear trend seen in A and B is genuine.

Analysis of A vs. stress shows that the relationship is linear. However, it is anticipated that although finite element analysis predicts linear behaviour, and this is consistent with experimental results, not all practical devices may exhibit this dependence and consequently the equation is preferably generalised as a $2^{nd}$ order polynomial.

Likewise, although B would appear to be essentially constant in the finite element analysis data, it is modelled as a $2^{nd}$ order polynomial to give high accuracy (and still give a closed form solution) with any likely behaviour of a real world sensor.

So we can produce equations for A and B as a function of stress, denoted A(s) and B(s) to indicate the functional dependence.

Modelling each as a $2^{nd}$ order polynomial gives $$A(s)=A_2 s^2+A_1 S+A_0 \quad \text{Equation (3)}$$

$$B(s)=B_2 s^2+B_1 S+B_0 \quad \text{Equation (4)}$$

Conventional best fit techniques can then be used to calculate optimum values for $A_0$ $A_1$ and $A_2$ and likewise for $B_0$, $B_1$ and $B_2$.

In exactly the same way we determine $C_0$, $C_1$, $C_2$, $D_0$, $D_1$ and $D_2$ for the equations $$C(s)=C_2 s^2+C_1 S+C_0 \quad \text{Equation (5)}$$

$$D(s)=D_2 s^2+D_1 S+D_0 \quad \text{Equation (6)}$$

Referring briefly back to equation 1, this can be re-arranged to make frequency the subject of the equation as follows $$(\text{freq}_{mode\ 1})^2 = A(s)/(\text{density} - B(s))$$

Thus, frequency is a non-linear function of stress and density. Even with a first order approximation for A(s) and a zero order approximation for B(s), this yields $$\text{freq}_{mode\ 1} = \text{SQRT}\{(A_1 S+A_0)/(\text{density}-B_0)\}$$

Thus it can be seen that the ratio of frequencies will have a non-trivial dependence on both stress and density. It will be appreciated that, particularly if a first order approximation is used for A(s) and B(s), this can be re-arranged to make stress the subject of the equation, and stress can be equated and eliminated to yield a solution for density directly. Even for second order approximations, an iterative solution can be found for density.

From the above, we know that at any particular stress, equation (1) tells us that if we know A and B, we can determine the density from the frequency. But because A and B are functions of stress and stress is unknown the density cannot directly be determined.

However, the same considerations apply to equation 2 and since the density obtained from equations 1 and 2 must be the same, we can equate equations (1) and (2). This leads to the following equality:

$$A(s)*(\text{freq}_{mode\ 1})^{-2}+B(s)=C(s)*(\text{freq}_{mode\ 2})^{-2}+D(s) \quad \text{Equation (7)}$$

Expanding out we have:

$$(A_2 s^2+A_1 S+A_0)*(\text{freq}_{mode\ 1})^{-2}+B_2 s^2 B_1 S+B_0=(C_2 s^2+C_1 S+C_0)*(\text{freq}_{mode\ 2})^{-2}+D_2 s^2+D_1 S+D_{0\ tm\ Equation}\ (8)$$

Everything in this equation is either known (the coefficients $A_0$ etc) or measured (the modal frequencies) except s, the unknown stress.

By rearranging and collecting terms, a quadratic in s is obtained which can be solved using the conventional formula: (for brevity $f_1$ denotes $\text{freq}_{mode\ 1}$ and $f_2$ denotes $\text{freq}_{mode\ 2}$)

$$S^2(A_2 f_1^{-2}+B_2-C_2 f_2^{-2}-D_2)+S(A_1 f_1^{-2}+B_1-C_1 f_2^{-2}-D_1)+(A_0 f_1^{-2}+B_0-C_0 f_2^{-2}-D_0)=0 \quad \text{Eqn (9)}$$

Since $A_0 \ldots D_2$ and $f_1$ and $f_2$ are all known quantities (the coefficients will have been stored for the meter and the frequencies measured) this is a simple quadratic in S, equivalent to $\alpha S^2+\beta S+\gamma=0$, to which the solutions are $S=(-\beta+/-\text{SQRT}(\beta^2-4\alpha\gamma))/2\alpha$, where $\alpha=(A_2 f_1^{-2}+B_2-C_2 f_2^{-2}-D_2)$, $\beta=(A_1 f_1^{-2}+B_1-C_1 f_2^{-2}-D_1)$ and $\gamma=(A_0 f_1^{-2} 30\ B_0-C_0 f_2^{-2}-D_0)$ This allows us to solve directly for S, giving two roots. Because the $2^{nd}$ order equations are so nearly linear, the two roots are a long way apart and only one is physically possible, so the other can be rejected by comparing to a range. In practice, it is found to be the same root every time which is the "real" solution, so there is no practical ambiguity. It will be appreciated that this method is equivalent to determining the point of intersection of the curves of FIG. 9. As an alternative approach, any of a number of known numerical methods may be employed to determine the intersection point. For example, a pair of values may be tried for both curves and an iteration performed until the error is within a desired range. One or more starting values may be taken from a stored value and once a meter is working, may be based on previously determined values to reduce the time taken for the iterative approach to converge. If an iterative approach is used, it may be as easy to determine density directly, if a measure of stress is not required.

Knowing s, it is straightforward to substitute into A(s) and B(s) and substitute these into equation (1) to determine the density.

It will be appreciated that by modelling A and B as functions of density and approximating, the equation could theoretically be solved directly to yield density; however, since A and B are physical constants of the meter primarily determined by stress, a more accurate result may be attained by the method described above.

It will also be noted that, based on the results of the finite element analysis (which is consistent with experimental data), it would be possible to approximate A as a linear function $(A_1 S+A_0)$ and/or B as a constant $(B_0)$. This would marginally simplify computation without significantly detracting from the results. However, since the quadratic approximation is simple to implement and may enable unknown factors in a real meter to be compensated for, the quadratic is preferred.

It will of course be appreciated that the above technique may operate in any desired units and absolute frequency need not be measured; if convenient pulsatance or a number which is a scaled version of frequency or even reciprocal frequency (time period for example) may be used in place of actual frequency as a measure of frequency, with appropriate scaling of values. Similarly measures of density and stress may be output in any desired form. Stress and/or density may be used to correct other measurements, for example measurements of fluid flow, which may be derived from the measurements, in particular in a mass-flow meter at least one of the modes will be used to determine flow rate based on a phase difference in a conventional manner—this may be corrected based on accurate knowledge of density or tension or both. Similarly, densities or tensions outside a desired range may be used to detect potential fault conditions, for example an empty meter or a fracture in the tube.

Comparing the above technique to the conventional approach of EP-A-701 107, two modal frequencies are determined and the ratio between these is assumed to indicate stress directly. However, this requires the meter to be designed such that this ratio is independent of density, which is not a trivial task and may place undesirable constraints on the meter design. It also assumes the stress is linearly related to the frequency ratio, whereas the results presented show this only to be an approximation. Thus the technique described above does not require the ratio to be independent of density and does not assume linear relationships between stress and modal frequencies and is therefore both more generally applicable and more accurate. It should be noted that even simplifying the above so that A is considered to be a linear function of stress and B is considered to be a constant results in a different formula to that of EP-A-701 107, as this does not suggest that the frequency ratio, as used in the prior art document, will be a linear function of stress.

A sensitivity analysis of the two techniques was performed in order to predict the errors from the various assumptions.

FIG. 14 shows the frequency ratio derived from the data presented herein. This matches FIG. 5A of EP-A-701 107 in magnitude and shape fairly well. It is noted that, in practice, it may not be possible to operate a meter with the tube in compression (as buckling may result), so we have not extrapolated to a compressive axial force. Although plotting the values alone suggest a nearly linear relationship and might lead one to assume that a linear approximation is appropriate, by plotting these together with a true line as in FIG. 14, it can be seen that the relationship is in fact significantly non-linear.

This in itself leads to errors in the stress determination. FIG. 15 shows this error as a function of the measured frequency ratio.

Since we know that the error due to ignoring the stress completely is approximately 100% full scale density error, it could be assumed that using this linear assumption as in EP-A-701 107 could bring that error down to less than +/−2%, which may be acceptable in many cases, provided the meter is designed to ensure that the variation of frequency ratio with density is negligible. However, using the techniques presented above, this error can surprisingly be reduced by a further factor of approximately 5, without significantly complicating processing; the example above simply requires solving a quadratic equation which is straightforward to implement, for example in the digital signal processor which is used to process the data. Furthermore, there are no such constraints on frequency ratios, which may be constant or may vary and need not even be measured. Thus, the technique disclosed above may yield significantly better accuracy and simplify meter design and construction by removing the need to adjust the meter to eliminate density dependence of the frequency ratio. To summarise, it can be assumed that the prior art technique is limited to a fundamental accuracy of about +/−2%, even with optimum meter design to reduce density dependence, and cannot readily be extended. The technique disclosed may achieve basic accuracies of the order of +/−0.5% or better requiring only solution of a simple quadratic and without requiring meter modification. If appropriate, higher order equations may be used, although the results shown do not suggest that this is necessary.

However, leaving aside this first shortfall in basic accuracy with the prior art technique, error sensitivity analysis is considered; it has been considered that a better basic accuracy may not be sufficient if the technique is highly sensitive to small measurement errors.

The straight line fit of the ratio (applying the prior art technique to the data presented herein) gives the following relationship:

Stress=(ratio−2.8799)/(−8.4002×10$^{-4}$)

Ratio is $f_2/f_1$

Numerically, $f_1$ is 217.26 and $f_2$ is 626.01 which in the above equation gives a stress of −1.7 MPa. However, this is simply due to the non-linear relationship as shown in FIG. 15. More importantly, if the influence of a small frequency change on f1 or f2, at nominal zero stress, is examined, it appears that the sensitivity of stress determination using the prior art technique to f1 or f2 is 15 or 5.5 MPa/Hz respectively.

The corresponding errors for the technique disclosed above are 11 and 3.2 respectively.

At a nominal 100 MPa stress, the prior art sensitivity is 14.3 and 5.1 respectively and the technique disclosed above presents a sensitivity of 13.1 and 3.9 respectively.

Thus, in addition to the better basic accuracy, the technique disclosed herein is surprisingly less sensitive to errors in frequency determination than the prior art technique. Moreover analysis suggests that this can be expected for a variety of designs. A measure of the error sensitivity can be visualised as being dependent to an extent on the angle with which the curves of FIG. 4 or 9 intersect, or the ratio of the slopes. Analysis suggests that this is likely to be similar in most cases.

Whilst the invention has been explained in terms of solving equations, it will be appreciated that, in a practical implementation, it is of course not necessary to go through the steps of plotting the various curves depicted. Instead, once the coefficients have been determined for a particular meter and stored, for example during an initial calibration phase (although results suggest that it may be satisfactory to store coefficients for a class of meters provided manufacturing tolerances are reasonable and still achieve high accuracy), it is straightforward to solve the quadratic equation for stress and then to obtain a value for density.

As mentioned above, a more sophisticated approximation than a second order fit may be employed if desired. Since the results given will be very accurate for most cases and the quadratic approach has the virtue of elegant simplicity to implement, these are not discussed in detail, and would not appear to be necessary in most cases. However, it is appreciated that, in certain designs, a higher order polynomial fit (or other approximation) may be appropriate and such equations may be solved by known numerical methods. This is straightforward to implement in practice; conventional microprocessors are readily available which can without difficulty perform sufficient iterations using known numerical techniques to solve a higher order polynomial fit to the accuracy required and with sufficiently frequent output readings (for example, a 1 GHz Pentium III processor can perform several million iterations each second and in practice a few hundred may be ample).

The results may also be converted into a function which yields stress and/or density directly as a function of the two input frequencies. For example, during calibration (either for an individual meter or for a class of meters, or even in a simulation), a number of stress and density values may be determined and the results plotted or stored to yield stress and density as 2-dimensional functions of the input frequency s(f1,f2) and ρ(f1,f2) respectively. These may be stored as numerical arrays or approximated by a polynomial or the like fit, from which the values may be obtained directly. Hence, references in this specification, which term includes the claims, to determining stress or density based on modelling the frequencies as functions of stress and density and solving are not intended to be limited to explicit solution as outlined above but are intended to encompass techniques having an equivalent effect. In particular, the actual determination of stress and density may simply use a look-up table or 2-d approximation function, values of which have previously been determined with reference to the modelling explained herein.

Although most useful in a straight tube meter, as discussed, the invention is not limited to meters of any particular geometry.

Many modifications of detail may be apparent. The features listed above may be provided independently unless otherwise stated. The appended abstract is incorporated herein by reference.

What is claimed is:

1. Use of measurements of resonant frequencies for two or more independent vibrational modes of a metering tube to obtain a measure of density of fluid in the metering tube compensated for variation of stress in the metering tube or to obtain a measure of stress in the metering tube, the method comprising wherein the ratio of said resonant frequencies is dependent on density and wherein the stress is determined as a non-linear function of ratio of said resonant frequencies.

2. Apparatus for obtaining a measure of stress in a fluid metering tube, the fluid having a density, the apparatus comprising:

exciter means for inducing first and second vibration modes in the tube and obtaining a first resonant frequency of the first vibration mode which is a first function of stress and density;

frequency measurement means for obtaining a second resonant frequency of the second vibration mode which is a second function of stress and density; and processing means for deriving said measure of stress from said first and second resonant frequencies based on determining possible pairs of values of stress and density corresponding to one of the first and second resonant frequency and selecting a pair of values based on the other of the first and second resonant frequencies.

3. Apparatus for obtaining a measure of density of a fluid in a metering tube, the tube being subjected to stress, the apparatus comprising:

exciter means for inducing first and second vibration modes in the tube and obtaining a first resonant frequency of the first vibration mode which is a first function of stress and density;

frequency determining means for obtaining a second resonant frequency of the second vibration mode which is a second function of stress and density; and processing means for deriving said measure of density from said first and second resonant frequencies based on modeling the fluid density as a first function of stress and the first resonant frequency and modeling the fluid density as a second function of stress and the second resonant frequency and solving to eliminate stress.

4. Apparatus according to claim 3 including processing means for deriving said measure of stress from said first and second resonant frequencies based on modeling the fluid density as a first function of stress and the first resonant frequency and modeling the fluid density as a second function of stress and the second resonant frequency and solving to determine stress as a function of said frequencies.

5. Apparatus according to claim 3, including iteration means for selecting the pair of values iteratively.

6. A method of obtaining a measure of density of fluid in a metering tube, the tube being subjected to a stress, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of density from said first and second resonant frequencies based on modeling the fluid density as a first function of stress and the first resonant frequency and modeling the fluid density as a second function of stress and the second resonant frequency and solving to eliminate stress.

7. A method according to claim 6, wherein the stress is first determined by modeling the fluid density as a first function of stress and the first resonant frequency and modeling the fluid density as a second function of stress and the second resonant frequency and solving to determine stress as a function of said frequencies.

8. A method according to claim 6 wherein the density is determined using an empirically determined function or, look-up table using previously calculated values reflecting said modeling.

9. A method according to claim 6, wherein density is determined without explicitly calculating stress.

10. A method according to claim 9, wherein density is determined iteratively.

11. A method of obtaining a measure of stress in a fluid metering tube, the fluid having a density, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of stress from said first and second resonant frequencies based on determining possible pairs of values of stress and density corresponding to one of the first and second resonant frequency and selecting a pair of values based on the other of the first and second resonant frequencies.

12. A method according to claim 11, wherein the pair of values is selected by equating the values and solving by modeling the fluid density as a first function of stress and the first resonant frequency and modeling the fluid density as a second function of stress and the second resonant frequency and solving to determine stress as a function of said frequencies.

13. A method according to claim 11, wherein the pair of values is selected iteratively.

14. A method according to claim 13, wherein an initial value for at least one of stress and density is selected based on a predetermined starting value.

15. A method according to claim 13, wherein an initial value for at least one of stress and density is selected based on a previously measured value.

16. Apparatus for obtaining a measure of stress in a fluid metering tube, the fluid having a density, the apparatus comprising:

exciter means for inducing first and second vibration modes in the tube and obtaining a first resonant frequency of the first vibration mode which is a first function of stress and density;

frequency measurement, means for obtaining a second resonant frequency of the second vibration mode which is a second function of stress and density; and processing means for deriving said measure of stress from said first and second resonant frequencies based on modeling the fluid density as a first function of stress and the first resonant frequency and modeling the fluid density as a second function of stress and the second resonant frequency and solving to determine stress as a function of said frequencies.

17. Apparatus according to claim 16 including mathematical processing means for solving a quadratic equation for stress with coefficients based on said first and second frequencies and stored values.

18. Apparatus according to claim 16 including second memory means for storing an empirically determined function or look-up table using previously calculated values reflecting said modeling.

19. Apparatus according to claim 16 including output means for outputting at least one of a measure of stress or a measure of density.

20. Apparatus according to claim 16 wherein the first and second vibration modes are substantially orthogonal.

21. Apparatus according to claim 16 further comprising means for detecting a potential fault or calibration inaccuracy based on said measure of stress or density or based on a torsional vibrational characteristic of the metering tube.

22. Apparatus according to claim 16 wherein the density is modeled by the following equations:

$$\text{Density} = A(s) * (\text{freq}_{mode\ 1})^{-2} + B(s)$$

$$\text{Density} = C(s) * (\text{freq}_{mode\ 2})^{-2} + D(s)$$

where $\text{freq}_{mode\ 1}$ and $\text{freq}_{mode\ 2}$ are said first and second resonant frequencies respectively and $A(s)$, $B(s)$, $C(s)$ and $D(s)$ are functions of stress.

23. Apparatus according to claim 22, wherein functions $A(s)$, $B(s)$, $C(s)$ and $D(s)$ are approximated by at least second order polynomials wherein $$A(s) = A_2 s^2 + A_1 s + A_0$$

$$B(s) = B_2 s^2 + B_1 s + B_0$$

$$C(s) = C_2 s^2 + C_1 s + C_0$$

$$D(s) = D_2 s^2 + D_1 s + D_0$$

where s represents stress and wherein at least $A_1$, $B_0$, $C_1$, and $D_0$ are non-zero co-efficients, the apparatus including first memory means for storing at least the non-zero co-efficients.

24. Apparatus according to claim 16 further comprising means for determining at least one fluid flow parameter from at least one vibration mode.

25. Apparatus according to claim 24, further comprising means for determining a measure of flow and adjusting said measure of flow based on the measure of stress or density.

26. Apparatus according to claim 16, including said metering tube.

27. Apparatus according to claim 26, wherein the metering tube is substantially straight or has low compliance.

28. Apparatus according to claim 26 wherein the tube is held in tension substantially within a predetermined range over a range of operating temperatures.

29. Apparatus according to claim 26, wherein the metering tube includes one or more loops or has high compliance.

30. A method of obtaining a measure of stress in a fluid metering tube, the fluid having a density, the method comprising inducing first and second vibration modes in the tube and obtaining a first resonant frequency of the first vibration mode which is a first function of stress and density; obtaining a second resonant frequency of the second vibration mode which is a second function of stress and density; and deriving said measure of stress from said first and second resonant frequencies based on modeling the fluid density as a first function of stress and the first resonant frequency and modeling the fluid density as a second function of stress and the second resonant frequency and solving to determine stress as a function of said frequencies.

31. A method according to claim 30, wherein stress is determined by iterative solution.

32. A method according to claim 30 wherein the stress is determined using an empirically determined function or look-up table using previously calculated values reflecting said modeling.

33. A method according to claim 30 further comprising outputting the measure of stress.

34. A method according to claim 30, further comprising using the measure of stress to derive a measure of fluid density.

35. A method according to claim 30 wherein if solving for stress or density produces more than one potential solution, solutions giving a value substantially outside a predetermined stress or density range are rejected.

36. A method according to claim 30, wherein the metering tube includes one or more loops or has high compliance.

37. A method according to claim 30 further comprising determining at least one fluid flow parameter from at least one vibration mode.

38. A method according to claim 30, further comprising determining a measure of flow and adjusting said measure of flow based on the measure of stress or density.

39. A method according to claim 30 further comprising detecting a potential fault or calibration inaccuracy based on said measure of stress or density or based on a torsional vibrational characteristic of the metering tube.

40. A method according to claim 30, wherein the ratio of said first and second resonant frequencies varies with density.

41. A method according to claim 30, wherein the stress is determined by solving a quadratic equation for stress with coefficients based on said first and second frequencies and stored values.

42. A method according to claim 41, wherein functions $A(s)$, $B(s)$, $C(s)$ and $D(s)$ are approximated by at least second order polynomials wherein $$A(s) = A_2 s^2 + A_1 s + A_0$$

$$B(s) = B_2 s^2 + B_1 s + B_0$$

$$C(S) = C_2 s^2 + C_1 s + C_0$$

$$D(s) = D_2 s^2 + D_1 s + D_0$$

where s represents stress and wherein at least $A_1$, $B_0$, $C_1$ and $D_0$ are non-zero co-efficients, wherein stress is determined by solving the equation:

$$S^2(A_2 f_1^{-2} + B_2 - C_2 f_2^{-2} D_2) + S(A_1 + f_1^{-2} + B_1 - C_1 f_2^{-2} - D_1) + (A_0 f_1^{-2} + B_0 - C_0 f_2^{-2} - D_0) = 0.$$

43. A method for use in determining a measure of stress or density comprising performing a method according to claim 30 for a plurality of values of stress and density and determining an empirical function or look-up table of values relating said first and second resonant frequencies to stress or density.

44. A method according to claim 43, further comprising storing said empirical function or look-up table in memory means.

45. A method according to claim 30, wherein the metering tube is substantially straight or has low compliance.

46. A method according to claim 45, wherein the measure of stress is a measure of tension or axial force in the tube.

47. A method according to claim 45 wherein the tube is held in tension substantially within a predetermined, range over a range of operating temperatures.

48. A computer program or computer program product comprising instructions for performing a method according to claim 30.

49. Apparatus comprising a signal processor of a flow meter arranged to operate in accordance with a computer program according to claim 48.

50. A flow meter comprising a signal processor according to claim 49 and a metering tube.

51. A method according to claim 30, wherein the density modeled by each function varies with a ratio of a first function of stress over frequency squared plus a second function of stress.

52. A method according to claim 51, wherein the second function is a zero order function.

53. A method according to claim 51, wherein the first function of stress is at least a first order function.

54. A method according to claim 53, wherein at least the first function is a second order function, preferably wherein both functions are approximated by second order polynomials.

55. A method according to claim 30, wherein the density is modeled by the following equations:

$$\text{Density} = A(s) * (\text{freq}_{mode\ 1})^{-2} + B(s)$$

$$\text{Density} = C(s) * (\text{freq}_{mode\ 2})^{-2} + B(s)$$

where $\text{freq}_{mode\ 1}$ and $\text{freq}_{mode\ 2}$ are said first and second resonant frequencies respectively and A(s), B(s), C(s) and D(s) are functions of stress.

56. A method according to claim 55, wherein functions A(s), B(s), C(s) and D(s) are approximated by at least second order polynomials wherein $$A(s) = A_2 s^2 + A_1 s + A_0$$

$$B(s) = B_2 s^2 + B_1 s + B_0$$

$$C(S) = C_2 S^2 + C_1 S + C_0$$

$$D(s) = D_2 s^2 + D_1 s + D_0$$

where s represents stress and wherein at least $A_1$, $B_0$, $C_1$, and $D_0$ are non-zero co-efficients.

57. A method according to claim 56, wherein the coefficients are obtained by fitting to empirically determined values.

58. A method according to claim 56 including retrieving the coefficients from a store.

59. A method according to claim 30 wherein the first and second vibration modes are substantially orthogonal.

60. A method according to claim 59 wherein the first and second modes have substantially different frequencies.

61. A method according to claim 59 wherein the first and second modes are spatially oriented in substantially orthogonal respective first and second spatial directions.

62. A method according to claim 61 wherein the tube has different vibrational properties in said first and second spatial directions, preferably wherein the tube is asymmetric, preferably having a rectangular or oval cross-section and/or wherein the tube is mounted to enhance or decrease bending stiffness in one of said spatial directions.

* * * * *